(12) United States Patent
Bujanover (10) Patent No.: US 7,588,929 B2
(45) Date of Patent: Sep. 15, 2009

(54) PRODUCTION OF BACTERIOPHAGE COMPOSITIONS FOR USE IN PHAGE THERAPY

(75) Inventor: Sergey Bujanover, Jerusalem (IL)

(73) Assignee: Phage Biopharm LLC, Aventura, FL (US)

( * ) Notice: Subject to any disclaimer, the term of this patent is extended or adjusted under 35 U.S.C. 154(b) by 0 days.

(21) Appl. No.: 10/538,599

(22) PCT Filed: Dec. 9, 2003

(86) PCT No.: PCT/IL03/01041

§ 371 (c)(1),
(2), (4) Date: Jul. 24, 2006

(87) PCT Pub. No.: WO2004/052274

PCT Pub. Date: Jun. 24, 2004

(65) Prior Publication Data

US 2007/0010001 A1   Jan. 11, 2007

Related U.S. Application Data

(60) Provisional application No. 60/431,723, filed on Dec. 9, 2002.

(51) Int. Cl.
| | | |
|---|---|---|
| C12Q 1/70 | (2006.01) | |
| C12Q 1/68 | (2006.01) | |
| G01N 33/554 | (2006.01) | |
| C12P 21/04 | (2006.01) | |
| A01N 63/00 | (2006.01) | |
| C12N 7/02 | (2006.01) | |
| G01N 33/00 | (2006.01) | |

(52) U.S. Cl. ............ 435/239; 435/6; 435/7.32; 435/71.1; 435/71.2; 435/5; 424/93.6

(58) Field of Classification Search ............ None
See application file for complete search history.

(56) References Cited

U.S. PATENT DOCUMENTS

| | | | | |
|---|---|---|---|---|
| 6,322,783 B1 * | 11/2001 | Takahashi | ............ | 424/93.6 |
| 6,482,632 B1 * | 11/2002 | Agrawal et al. | ............ | 435/235.1 |
| 2001/0026795 A1 | 10/2001 | Merril et al. | ............ | 424/93.21 |
| 2002/0001590 A1 | 1/2002 | Kelly et al. | ............ | 424/184.1 |
| 2002/0044922 A1 | 4/2002 | Mardh | ............ | 424/93.6 |
| 2002/0058027 A1 | 5/2002 | Nelson et al. | ............ | 424/94.63 |
| 2004/0091856 A1 * | 5/2004 | Pelletier et al. | ............ | 435/6 |

FOREIGN PATENT DOCUMENTS

| | | |
|---|---|---|
| WO | WO 00/69269 | 11/2000 |
| WO | WO 02/07742 | 1/2002 |

OTHER PUBLICATIONS

Swanstrom and Adams, Agar Layer Method for Production of High Titer Phage Stocks, 1951, Proceedings of the Socieity for Experimental Biology and Medicine, pp. 372-375.*

* cited by examiner

*Primary Examiner*—Gary B Nickol
*Assistant Examiner*—Benjamin P Blumel
(74) *Attorney, Agent, or Firm*—Heslin Rothenberg Farley & Mesiti P.C.

(57) ABSTRACT

The present invention relates to the use of bacteriophages to treat infectious diseases. The invention provides a method for intermediate to large scale commercial production of bacteriophage compositions, wherein the method reduces the production volume and elevates production yield. The invention further relates to improved bacteriophage compositions comprising specific sugars that reduce or abolish the bacterial phage-neutralizing activity.

23 Claims, 3 Drawing Sheets

FIG. 1

Preparation of semi-solid composition:
- 10 isolated phage plaques
- $10^9$ to $10^{10}$ cfu of the matching bacterial strain
- 60 ml of rich medium at agar concentration of 0.27%

Tray preparation:
Spreading 250 ml of rich medium at agar concentration of 1.5% on 60x60x5 cm plastic trays. 25 trays are prepared.

Phage growth:
- Spreading 60 ml of the semi-solid culture medium over the solid phase on each tray.
- Incubating all 25 trays in an industrial incubator at 37°C for 16-18 h, until maximal bacterial lysis is obtained.

Collecting phage lysate:
- Scrapping the semi-solid composition from each tray
- Mixing the scraped lysate from each tray with 200 ml of rich medium.
- Mixing the slurry vigorously (about 300 ml) for 30 seconds
- Centrifuging the slurry at 11G for 30 min at 4°C.
- Collecting the supernatant comprising the crude bacteriophage extract
- Subjecting the pellet to multiple serial extractions.
- Total volume (from 25 trays) of the obtained crude phage extract is about 55 liters at a titer of $10^{12}$

PRODUCTION OF BACTERIOPHAGE COMPOSITIONS FOR USE IN PHAGE THERAPY

CROSS REFERENCE TO RELATED APPLICATIONS

This application is a 371 filing of PCT International application no. PCT/IL2003/001041 filed Dec. 9, 2003 and published in English as WO 2004/052274 A2 on Jun. 24, 2004 which claims priority of U.S. provisional application Ser No. 60/431,723 filed Dec. 9, 2002, the disclosures of which are hereby incorporated by reference in their entirety.

FIELD OF THE INVENTION

The present invention relates to the use of bacteriophages to treat infectious diseases, more particularly, to a method for production of bacteriophage compositions, said method reducing the production volume and elevating production yield. The invention further relates to improved bacteriophage compositions comprising specific sugars that reduce or abolish the bacterial phage-neutralizing activity.

BACKGROUND OF THE INVENTION

Bacteriophages (phages) are a phylum of viruses that infect bacteria, and are distinct from the animal and plant viruses. Phages can have either a "lytic" life cycle, a "lysogenic" life cycle that can potentially become lytic, or a "non-lytic" life cycle. Phages replicating through the lytic cycle cause lysis of the host bacterial cell as a normal part of their life cycles. Phages replicating through the lysogenic cycles are called temperate phages, and can either replicate by means of the lytic life cycle and cause lysis of the host bacterium, or they can incorporate their DNA into the host bacterial DNA and become noninfectious prophages.

The natural capability of phages to infect and kill bacteria, together with the specificity of the phage-bacterial interactions, is the basic phenomena on which the concept of phage therapy is built. Therefore, phages that possess lytic life cycle are the most suitable candidates for phage therapy.

Phage therapy was first proposed by D'herelle (D'herelle 1922. The bacteriophage: its role in immunity. Williams and Wilkens Co. Waverly Press Baltimore USA), showing promise but also arousing much controversy. Since the introduction of antibiotics in the 1940s, little attention was paid to this field of therapeutics, especially in the Western world. The main reason for this lack of interest was the fact that none of the potential experimental therapeutic uses has resulted in the formulation of an efficacious bacteriophage composition, i.e., one that is sufficiently virulent, non-toxic, host-specific, and yet with a wide enough host range to be of practical use.

The extensive use of antibiotics has led to an increase in the number of bacterial strains resistant to most or all available antibiotics, causing increasingly serious problems and raising widespread fears of return to a pre-antibiotic era of untreatable infections and epidemics.

The newfound ability to sequence entire microbial genomes and to determine the molecular bases of pathogenicity may open new avenues for treating infectious diseases, but other approaches are also being sought with increasing fervor. One such approach is the technology of bacteriophage therapy, which is attracting renewed attention in the West as a potential weapon against drug-resistant microbes and hard-to-treat infection (Stone R 2002 *Science* 298:728-731).

With the fast development in the field of molecular biology, much attention has been devoted to phages as research tools. Today phages are widely used for the identification of bacteria types and in various molecular biology techniques, and good laboratory practice is available for the isolation of highly pure phage compositions.

These newly developed techniques have been also used in the field of phage therapy. For example, International Patent Application No. WO 00/69269 discloses the use of certain phage strain for treating infections caused by Vancomycin-sensitive as well as resistant strains of *Enterococcus faecium*, and International Patent Application No. WO 01/93904 discloses the use of bacteriophage, alone or in combination with other anti-microbial means, for preventing or treating gastrointestinal diseases associated with the species of the genus *Clostridium*.

US Patent Application No. 2001/0026795 describes methods for producing bacteriophage modified to delay inactivation by the host defense system, and thus increasing the time period in which the phage is active in killing the bacteria.

US Patent Application No. 2002/0001590 discloses the use of phage therapy against multi-drug resistant bacteria, specifically methicillin-resistant *Staphylococcus aureus*, and International Patent Application No. WO 02/07742 discloses the development of bacteriophage having multiple host range.

The use of phage therapy for the treatment of specific bacterial-infectious disease is disclosed, for example, in US Patent Application Nos. 2002/0044922; 2002/0058027 and International Patent Application No. WO 01/93904.

However, commercial scale production of bacteriophage compositions for therapeutic use is still limited. In current techniques, the titer of the phage composition is low, usually in the range of $10^9$-$10^{11}$ pfu/ml on a laboratory scale, and $10^7$-$10^9$ on a commercial scale, whereas the titer typically required for phage therapy is $10^{12}$ pfu/ml. Additionally, to reach the desirable titer, very large volumes of liquid are required.

As described herein below, the dosage for phage therapy is in the range of $10^6$ to $10^{13}$ pfu/Kg body weight/day, with $10^{12}$ pfu/Kg body weight/day suggested to be a preferable dosage. According to the currently common liquid culture methods for phage growth, reaching one daily dose of bacteriophage therapy per person would require a liquid volume of 5-10 liters. Commercial production of phage stock composition of one specific phage type would therefore involve growth at volumes of thousands of liters with the need of multiple uses of large-volume fermenters.

The large volume of liquid also requires the use of large fermenters that are difficult and expensive to operate. Moreover, the subsequent processes of phage purification, at least in part, are also performed with large liquid volumes, making working under good manufacturing practice (GMP), necessary for the production of pharmaceutical compositions, very hard to achieve.

In fact, a common estimation is that the clinical trials in the field of phage therapy would be very expensive, the reason being the benefit of using a phage "cocktail" for efficient treatment, with the need to prepare each phage separately in the special GMP facilities required for FDA approval. This, in turn, means that phage therapy will be relatively expensive, at least initially.

Therefore, there is a recognized need for, and it would be highly advantageous to have a method for commercial production of phage compositions that elevates yield titer, reduces manufacturing volume and enables the application of low-volume well-developed purification processes to the obtained phage extract.

SUMMARY OF THE INVENTION

It is an object of some aspects of the present invention to provide methods eliminating the need for fermenters in the manufacture of a bacteriophage composition or a bacteriophage cocktail on a scale suitable for a commercial production, more particularly to a method for the large scale commercial production of bacteriophage stock compositions having a titer of at least $10^{11}$ pfu/ml, obtainable using a total operating volume in the range of less than 100 liters per production run, or even 70 liters or less.

The methods of the present invention are not limited to a specific combination of bacterium and phage, and may be employed for the production of any bacteriophage stock composition, preferably for therapeutic uses.

According to some aspects of the present invention there is provided a method adapting techniques hitherto used on a laboratory scale, for a commercial large-scale growth of bacteriophage in a semi-solid medium. According to the present invention, the specific semi-solid phase of the medium creates favorable conditions for phage growth, leading to a high titer, reducing the operating volume by about two orders of magnitude and eliminating the need to use large-volume fermenters. According to preferred embodiments the initial operating volume, calculated as the volume of the semi-solid medium in which the phage are propagated, is no more than 10-20 liters. According to some preferred embodiments the initial volume of the semisolid medium is no more than 5-10 liters.

Propagation of bacteriophage within semi-solid hydrocolloid media on a laboratory scale is well known in the art. It is herein disclosed for the first time that the titer obtainable and the ease of recovery of the bacteriophage from such media is unexpectedly enhanced greatly if the semi solid medium comprises less than 0.5% hydrocolloid, preferably less than 0.3% hydrocolloid.

According to one embodiment, the present invention discloses a method for the intermediate to large scale production in a semi-solid culture medium of stock compositions of bacteriophage having a titer of at least $10^{11}$ pfu/ml and a total yield of at least $10^{15}$ total pfu comprising:

a. growing bacteriophage in a semi-solid culture medium comprising a pre-incubated mixture of at least one bacterial strain and at least one phage type, further comprising a hydrocolloid at a concentration below 0.5%;

b. incubating the semi-solid culture medium to reach bacterial lysis, thereby obtaining a phage lysate; and c. extracting a crude bacteriophage extract from the semi-solid culture medium, using an extraction medium.

The total operating volume per production run is defined herein as the volume of the semi-solid hydrocolloid growth medium, plus the entire volume of the extractions performed according to the methods of the invention. According to one embodiment, the volume of the extraction medium is 20 to 100 fold the volume of the semi-solid culture medium. These volumes of semi-solid hydrocolloid medium are conveniently extractable at titers in excess of $10^{10}$ pfu per ml extract in typically, a total extraction volume of about 100 liters. Typically, the titers will remain in the order of $10^{11}$, preferably $10^{12}$ per ml extract, thus providing a yield in excess of $10^{16}$ per production run. Clearly these volumes could be increased further, without departing from the essence of the teachings of the present invention. The convenience of working in production volumes that are in the range of tens of liters will be apparent to those skilled in the art. Nevertheless, it is to be understood that larger volumes are expressly included in the scope of the invention.

According to one embodiment the semi-solid culture medium comprises hydrocolloid at a concentration below 0.3%.

According to one currently preferred embodiment the semi-solid culture medium comprises hydrocolloid at a concentration of 0.25%-0.30%.

According to one embodiment, the hydrocolloid is selected from the group consisting of agar, agarose, starch, pectin, carrageenan, alginate, gelatin, gellan, konjak mannan, xanthan and gum, or a combination thereof. According to one currently preferred embodiment the hydrocolloid is agar. According to one currently most preferred embodiment the semi-solid culture medium comprises agar at a concentration of 0.25%-0.30%.

According to one embodiment, the semi-solid culture medium further comprises rich medium suitable to the bacterial host type.

According to one currently preferred embodiment, the pre-incubated mixture comprises bacteria and bacteriophage at a ratio of about $10^{8}$-$10^{9}$ bacterial colony-forming units (cfu) to one bacteriophage plaque.

According to another embodiment, the semi-solid culture medium is supported by a solid phase. The supportive solid phase may have any suitable geometric form and comprise any material as long as the bacteriophage growth within the semi-solid culture medium is sustained or improved as compared to its growth without the supportive solid phase. Typically, the volume of the supportive solid phase is from about two to ten fold the total volume of the semi solid medium that it is intended to support.

According to one embodiment, the semi-solid culture medium is layered on top of a first supportive solid phase bottom layer to form a second top layer. According to one embodiment, the supportive solid phase comprises hydrocolloid at a concentration range of 1.0-2.0%. According to another embodiment, the supportive solid phase comprises agar at a concentration range of 1.0-2.0%.

According to yet another embodiment the supportive solid phase and the semi-solid culture medium are incubated to reach bacterial lysis, thereby obtaining a phage lysate. According to one currently preferred embodiment, incubation time is in the range of 12-24 h, preferably 14-18 h, and incubation temperature is typically 37° C. Suitable culture conditions and media for bacteria and phages are well known in the art. The advantage of the present invention over the methods known in the art is the ability to culture the bacteriophage and obtain a concentrated lysate on a commercial scale within a semi solid hydrocolloid medium thereby reducing production volumes and lowering costs.

According to one embodiment the bacteriophage stock composition is obtained by sequential serial extractions comprising the steps of:

a. collecting the semi-solid culture medium;

b. adding fresh medium to the semi-solid culture medium to obtain a slurry;

c. mixing the slurry intensively;

d. centrifuging the slurry to obtain a supernatant comprising a crude bacteriophage extract;

e. collecting the obtained crude bacteriophage extract; and f. repeating the aforementioned steps until the phage titer in the crude bacteriophage extract is at or below $10^{10}$ pfu/ml; wherein a crude bacteriophage extract having a total phage count of at least from about $10^{15}$ to about $10^{16}$ is obtained from about one liter of semi solid composition.

Typically, the phage titer reaches a value of $10^{10}$ pfu/ml or below after multiple serial extractions, commonly after 5-15 sequential extractions. The crude extract obtained by sequential extractions may be combined or kept separate. The titer of each preparation is at least $10^{11}$ pfu/ml, preferably in the range of $5\times10^{11}$ to $10^{12}$ pfu/ml. Typically, the phage titer declines to a value of about $10^{10}$ pfu/ml after 5-15 sequential extractions. The cumulative volume used for such extractions is typically less than 100 liter, or even less than 70 liter.

According to another embodiment a modified, one step extraction procedure is employed, comprising the steps of:

a. collecting the semi-solid culture medium;

b. adding fresh medium to the semi-solid culture medium to obtain a slurry;

c. mixing the slurry vigorously at low temperature for at least 12 h;

d. centrifuging the slurry to obtain a supernatant comprising a crude bacteriophage extract; and e. collecting the obtained crude bacteriophage extract; wherein a crude bacteriophage extract having a phage count from about $10^{15}$ to about $10^{16}$ is obtained from about one liter of semi solid composition.

Typically, the volume of the fresh medium added to the semi-solid culture medium is in the range of 70-100 liters or even less. According to one embodiment the semi-solid culture medium is vigorously mixed at a temperature of 4° C. for about 14-20 h.

According to yet another embodiment, the crude bacteriophage extract is purified from bacterial debris and endotoxins. One major reason for the slow progress in the development of phage therapy is the obligatory requirement to obtain a preparation essentially free of toxins. The ambiguous results obtained with phage therapy in the past were partly due to the presence of endotoxins in the preparation, such that the toxin masked the beneficial effect of the bacteriophage or even caused adverse effects. According to the present invention, purification may be performed by methods known to one skilled in the art. However, the high phage titers per volume obtained by the method of the present invention advantageously makes it possible to use well-developed low-volume purifying methods. Such methods include fractionation by Polyethylene glycol (PEG), CsCl gradient centrifugation, filtration, ultra-filtration, column chromatography, etc. The purified bacteriophage stock composition may be further lyophilized.

According to another aspect the present invention provides bacteriophage compositions efficient in killing host bacteria present during an infection, comprising non-toxic bacteriophage stock compositions further comprising substances that reduce or abolish bacterial phage-neutralizing activity.

During the adsorption of phages to bacterial surface, the bacteria may activate a mechanism for neutralizing phage propagation. This mechanism depends on the specific structure and composition of the bacterial receptor, and lipopolysaccharides (LPS), lipoproteins and phospholipids have been shown to play a role in the process of bacterial phage neutralization. Such neutralization process may significantly reduce the efficacy of phage therapy, by reducing the actual phage titer coping with the infectious bacteria Proteins, sugars or lipids that block the neutralizing determinants within the bacterial receptor can inhibit phage inactivation by the bacteria, and therefore may be used to enhance phage virulence.

According to one embodiment the present invention provides a bacteriophage composition comprising non-toxic bacteriophage stock compositions, further comprising at least one sugar that reduces or abolishes bacterial phage-neutralizing activity.

According to another embodiment, the inhibitory sugar is selected from the group consisting of N-acetyl-D-glucosamine, 2-deoxy-D-glucose, D-glucosamine, D-fructose, D-galactose, lactose, D-mannose, maltose, L-rhamnose, D-xylose, cellobiose (a disaccharide obtained from a partial hydrolysis of cellulose), and sucrose.

According to one embodiment, the present invention provides a bacteriophage stock composition comprising purified *Pseudomonas aeruginosa* bacteriophage stock composition and at least one inhibitory sugar selected from the group consisting of D-glucosamine, D-mannose and L-rhamnose. According to one currently preferred embodiment D-glucosamine is at a concentration range of 10-100 mM and D-mannose and L-rhamnose are at a concentration range of 100-1000 mM.

The present invention in explained in greater details in the description, figures, and claims below.

BRIEF DESCRIPTION OF THE FIGURES

FIG. 2 shows a schematic diagram of intermediate-scale production of bacteriophage stock compositions.

DETAILED DESCRIPTION OF THE INVENTION

The present invention relates to the field of phage therapy and pharmaceutical compositions comprising bacteriophages for use in treatment of human diseases. The concept of phage therapy, which was a common subject for research and clinical trials in Eastern Europe during the middle of the $20^{th}$ century, has gained renewed attention in the last decade.

There are several basic reasons why the concept of bacteriophage therapy for human or veterinary use has not been reduced successfully to practice: (i) the efficacy of phage therapy was shown to be marginal or even negligible; (ii) unacceptable toxic side effects have been observed, mainly due to the use of bacteriophage compositions contaminated with bacterial debris typically containing toxins; (iii) better alternatives, such as conventional chemical antibiotics, were already developed; (iv) appearance of new phage-resistant bacterial strain due to activation of the bacterial defense system upon introduction of the phage; and (v) fast removal of the bacteriophage from the body once the composition was injected or ingested, before the phage could arrive at the target site. The intensive research in the field of molecular biology, which employs bacteria and phages as a research tool, has advanced practical knowledge on bacterial-phage interactions and revealed new techniques that may be utilized to overcome at least part of the above described difficulties in the development of phage therapy to a reliable therapeutic tool.

In this context, the present invention provides a method for the commercial intermediate to large-scale production of bacteriophage stock compositions, in which each step is easy to perform, does not require large operating volumes, and is therefore highly compatible for stringent validation.

Reduction of the concept of phage therapy to practice requires the development of bacteriophage stock compositions that are host specific and yet has a broad enough host range to be of practical use, virulent, non-toxic and ready for formulation with pharmaceutically acceptable vehicles that can be administered to a subject suffering from bacterial infection. As used herein, a "broad enough host range" refers to a bacteriophage that is capable of killing bacteria from a variety of different hosts. The term "virulent" refers to a bacteriophage that is capable of effectively killing bacteria from a wide host range, namely that is capable of killing bacteria at a lower concentration compared to a non-virulent phage.

Production of pharmaceutical compositions comprising phages for use in phage therapy should follow several basic steps, including: phage typing to establish susceptibility of the pathogenic bacteria; selecting the correct phage or phage panel; picking a single plaque for each phage type to ensure uniform preparation; obtaining a high phage titer; collecting the phage; removing host bacteria from the phage crude extract; purifying the bacteriophage crude extract from endotoxins and other bacterial debris.

The arrest in development of phage therapy can be attributed in part to the limited technologies used during these processes, resulting in endotoxin-contaminated, not highly specific pharmaceutical compositions. The reduced production volume achieved using the methods of the present invention overcomes problems encountered previously in technologies used for obtaining bacteriophage stock compositions. In other words, using significantly smaller production volumes for commercial scale bacteriophage compositions permits utilization of well developed methods as are known in the art to achieve purified or refined stock compositions of bacteriophage.

The methods provided by the present invention for culturing bacteriophages in order to obtain bacteriophage stock compositions are based on growing the bacteriophage on a commercial scale in a semi-solid medium, wherein the specific semi-solid phase used for the culture medium creates favorable conditions for phage growth, leading to a high titer in a relatively low volume. According to preferred embodiments the initial operating volume, calculated as the volume of the semi-solid medium in which the phage are propagated, is no more than 10-20 liters. According to some preferred embodiments the initial volume of the semi-solid medium is no more than 5-10 liters.

Known methods of culturing stock compositions of bacteriophages on a laboratory scale involve one of two alternate techniques. According to one technique, phages are grown in a liquid medium. Alternatively, seed cultures for inoculation are cultured in semi-solid agar on a plate of solid agar. Nowhere in the art to which this invention pertains has it been taught or suggested that these methods are suitable to scale up for commercial quantities in a single production run. The method of the present invention unexpectedly shows that propagating a bacteriophage in a semi-solid composition comprising less than 0.5% hydrocolloid, preferably less than 0.3% hydrocolloid, results in an easy to extract, high titer bacteriophage extract.

Hitherto, scaled up production of bacteriophage stock compositions, whether in the laboratory or for clinical applications is performed in liquid cultures. Applying these known methods to large-scale commercial scale would require the use of very large fermenters. As each phage strain should be grown separately and under stringent sterile conditions, large and expensive environmentally controlled facilities would be required. The methods of the present invention eliminate the need to use fermenters, and therefore significantly simplify the commercial production of bacteriophage compositions and bacteriophage cocktails.

The term "high titer" as used herein refers to a bacteriophage titer of at least $10^{11}$ pfu/ml.

As used herein, the term "intermediate scale production" refers to production in volumes up to 100 liter. The term "large scale production" refers to production in volumes up to 2,000 liters.

According to one embodiment, the present invention provides a method for the intermediate to large scale production in a semi-solid culture medium of stock compositions of bacteriophage having a titer of at least $10^{11}$ pfu/ml and a total yield of at least $10^{15}$ total pfu consisting essentially of:

a. growing bacteriophage in a semi-solid culture medium comprising a pre-incubated mixture of at least one bacterial strain and at least one phage type, further comprising a hydrocolloid at a concentration below 0.5%;

b. incubating the semi-solid culture medium to reach bacterial lysis, thereby obtaining a phage lysate; and c. extracting a crude bacteriophage extract from the semi-solid culture medium by an extraction medium.

As defined herein, the total operating volume per production run is the volume of the semi-solid culture medium plus the volume required for extracting the bacteriophage from the semi-solid hydrocolloid composition according to the methods described in the present invention. According to one embodiment, the volume of the extraction medium is 20 to 100 fold the volume of the semi-solid culture medium.

The method of the present invention can further comprise other steps for improving the quality of the bacteriophage stock composition or facilitate the production procedure, including, but not limited to steps for purification, formulation, automation and the like.

The present invention contemplates use of any host bacterium that has stable reproduction and does not produce a toxin that has deleterious effects either on the bacteriophage or in the lysate recipient. Determination and selection of such bacteria is performed using techniques known to those skilled in the art and includes testing for the absence of toxins particularly: alpha toxin, beta toxin, delta toxin, gamma toxin, enterotoxins A, B, C, and D, Toxic Shock Syndrome Toxin (TSST), exfoliatins A and B, leukocidin, fatty acid modifying enzyme, and hemolysins. Testing also includes tests for stability and reproducibility of lysates generated by the phage-induced lysis, long-term sensitivity of the bacterial strains, and continued susceptibility of the bacteria to lysis by phages without the appearance of phage-resistant colonies.

According to one embodiment, the host-specific, non-toxic and purified bacteriophage stock compositions of the invention can be prepared by growing the phages in the presence of a microorganism including, inter alia, *staphylococci, hemophili, helicobacter, mycobacterium, streptococci, neisseria, klebsiella, enterobacter, proteus, bacteroides, pseudomonas, borrelia, citrobacter, escherichia, salmonella, propionibacterium, treponema, shigella, enterococci* and *leptospirex*. Preferably the microorganism includes, inter alia, *Staphylococcus aureus, Staphylococcus epidermidis, Helicobacter pylori, Streptococcus pneumoniae, Streptococcus mutans, Streptococcus oralis, Streptococcus parasanguis, Streptococcus pyogenes, Streptococcus viridans*, Group A *streptococcus* and *anaerobic streptococcus, Hemophilus influenzae, Shigella dysenteriae, Mycobacterium tuberculosis, Mycobacterium leprae, Mycobacterium asiaticum, Mycobacterium intracellulare, Mycoplasma pneumoniae, Mycoplasma hominis, Neisseria meningitidis, Neisseria gonorrhea, Klebsiella pneumoniae, Pseudomonas aeruginosa, Propionibac-*

*terium acnes, Treponema pallidum, Treponema pertanue, Treponema carateum, Escherichia coli, Salmonella typhimurium, Borrelia burgdorferi, Leptospirex,* such as *Leptospirex hemoragia Citrobacter fruendii*. More preferably, the microorganism is selected from any one of *staphylococci, streptococci, citrobacter, escherichia* and *klebsiella*, and most preferably, the microorganism is selected from *Staphylococcus aureus, Streptococcus pyogenes, Klebsielia oxytoca, Escherichia coli* and *Citrobacter fruendii*.

The present invention further contemplates use of any bacteriophage that stably reproduces in a selected bacterial strain and does not result in the production of a significant amount of a toxin or another component that has deleterious effects either on the host bacteria or on the mammal receiving the resulted lysate. Determination and selection of such bacteriophages include testing for long-term stability in a general host strain, long term persistence of virulence, stability and reproducibility of lysis and reproducibility of resultant lysates. The host strain is a strain which is sensitive to the lytic properties of the bacteriophage.

Various mechanisms can be used to select bacteriophage stock compositions that are virulent and therefore suitable for use in phage therapy. Initially, however, bacteriophage extract must be derived from microorganisms that can be effected using methods known in the art. (See, American Type Culture Collection Catalogue Of Bacteria And Bacteriophages, 18th Edition, pages 402-411 1992). For example, samples can be collected from individuals who suffer from a bacterial infection. Various samples can be taken from various places on the body including the throat, blood, urine, feces, spinal fluid, nasal mucosa, skin, washings from the larynx and trachea, and the like. Sample sites can be selected depending upon the target organism. For example, a throat swab likely would be used to collect a sample of a given strain of *streptococcus*, a skin culture likely would be used to collect a sample of a given strain of *staphylococcus*, a spinal fluid or blood sample likely would be used to collect a sample of *Neisseria meningitidis*, a urine sample can be used to collect samples of *E. coli*, and the like. Those skilled in the art are capable of obtaining an appropriate sample from the respective locus, given the target organism. Alternatively, bacterial strains can be obtained from various laboratories including those available from the National Institutes for Health (NIH), the ATCC and the like.

The specific bacteria-bacteriophage combination can then be further selected according to the intended use. For example, if the desired use is to provide immunity for staphylococcal infections, one or more strains of staphylococcal bacteria are used as the bacterial host organisms. In this same example, one or more bacteriophages that are specific for staphylococcal bacteria, or are at least capable of having a productive infection in staphylococcal bacteria, are used to create the staphylococcal lysate. Alternatively, one bacterial strain may be grown to produce a bacterial culture or bacterial broth and then separate aliquots of the bacterial culture are each infected with a different bacteriophage to create individual lysates. These individual lysates may be used individually or combined to form compositions. Another option is to use different bacterial strains and then infect each strain with the same bacteriophage to yield lysate compositions that can be used individually or combined to form compositions. Still alternatively, different bacterial stains that are each infected with different bacteriophages and the resulting lysates are used individually or in combination to form compositions.

Selected bacterial strains are purified, and colonies of the bacteria are grown using conventional methods. When a bacterial organism is identified from any of the aforementioned sources, it is preferably grown in pure culture and frozen for storage at about −20° C., −70° C. or −80° C. These organisms can be frozen using conventional methods. A particularly preferred method for freezing bacterial samples includes preparing overnight cultures of bacterial isolates, and then adding about 400 μl of a sterile 80% glycerol to about 1 ml of overnight culture. The storage tubes as exemplified by microtubes then can be labeled and stored at −20° C., −70° C. or −80° C.

These inoculate samples then can be used to generate the bacteriophage stock compositions by dispersing the sample in a solution, for example, a phosphate buffered saline solution, and then filtering the solution through a very small pore size filter to retain the target organism and permit the bacteriophage to pass through. Typically, a filter having a pore size in the range of from about 0.01 to about 1 μm can be used, preferably, from about 0.1 to about 0.5 μm and more preferably from about 0.2 to about 0.4 μm.

Bacteriophage stock compositions can then be generated by growing the phage in a medium containing the target organism with periodic tittering. The bacteriophage samples are taken periodically, preferably about every 2 hours and the quantity of bacteriophage tittered. Those skilled in the art are capable of growing bacteriophage in the bacterial host using conventional methods. As a non-limiting example, the bacteriophage stock composition of the present invention is obtained by culturing *Pseudomonas aeroginosa* in a liquid medium, spreading the culture on a plate and propagating the selected phage on the *P. aeroginosa* culture, as exemplified herein below. The phage-bacteria mixture is then directly added to the semi-solid culture medium according to the present invention for the production of bacteriophage stock compositions at a commercial scale.

Growth of bacteriophage on plates comprising a layer of a solid phase (bottom layer) and a layer of semi-solid phase (top layer) is a known procedure to one skilled in the art. Such methods are used when localization of bacteriophage on the solid layer is required for isolating a specific, single phage from the plate. For this purpose, phage plaques should be separate from one another, namely, low phage titer should be maintained. The commonly used procedure for obtaining such plates is to use an agar concentration of 1.2-1.5% to obtain the solid layer and an agar concentration of 0.6% in the semi-solid medium. This method is highly adequate for isolating a specific, virulent bacteriophage as defined herein above.

However, when producing bacteriophage compositions for treating a subject suffering from bacterial infection, a high phage titer should be obtained. As is known in the art, administration of therapeutically effective bacteriophage compositions can be performed by many routes, including but not limited to oral, aerosol, nasal spray, intravenous, intramuscular, intraperitoneal, intrathecal, vaginal, rectal and topical administration. Nevertheless, in any route chosen, the titer of the phage should be at the range of $10^{10}$ to $10^{13}$ pfu/Kg body weight/day, preferably about $10^{11}$ to $10^{12}$ pfu/Kg body weight/day. Such high treatment titer requires, as described herein above, efficient methods for producing high titer bacteriophage compositions.

The novel step in the method described in the present invention is the use of a semi-solid composition comprising hydrocolloid at a low concentration, specifically a concentration below 0.3%, preferably at a concentration of 0.25%-0.30%. This hydrocolloid concentration enables high replication rate of the phage, leading to a high titer of at least $5 \times 10^{11}$ phage/ml, typically to a titer of $10^{12}$ phage/ml after multiple serial extractions as exemplified herein below. Applying this method can therefore meet with the primary requirements of commercial production of the present invention, namely high titer and low operating volumes.

The bacteriophage yield according to the method of the present invention is in the order of magnitude of $10^{15}$-$10^{16}$ phages per one liter of semi-solid culture medium, typically extracted in a volume of 10-50 liters. In previously used methods of growth in a liquid culture, 1000 liters of liquid are required to reach the same order of magnitude of $10^{16}$ phages. Therefore, the method of the present invention reduces the operating volume by a factor of at least 200 compared to growth in a liquid. Nevertheless, it is to be understood that the operating volumes described herein are not intended to limit the volumes that may be used while operating the method of the present invention, and larger volumes are explicitly included in the scope of the invention.

The semi-solid composition of the present invention may comprise any hydrocolloid that is inert in regards to the bacterial and bacteriophage growth. Typically, the hydrocolloid is selected from the group consisting of agar, agarose, starch, pectin, carrageenan, alginate, gelatin, gellan, konjak mannan, xanthan and gum, or a combination thereof.

Phage lysate is not the end product for phage therapy. As described herein, it is necessary to purify the phage lysate from any remained bacteria, endotoxins or other debris, to obtain non-toxic, efficient bacteriophage composition to be used in phage therapy. By reducing dramatically the operating volume, the method of the present invention provides a crude bacteriophage extract suitable for further purification by many methods known in the art, which can be performed only at relatively small volumes. The suitable methods are well known in the art as disclosed for example in US Patent Applications Nos. 2001/0026795; 2002/0001590; U.S. Pat. Nos. 6,121,036; 6,399,097; 6,406,692; 6,423,299; International Patent Application No. WO 02/07742, among others.

Throughout this description, the expression "purified" denotes a bacteriophage stock composition that contains substantially no toxins, (no endotoxins) preferably less than 1.0% by weight of toxins (endotoxins) and more preferably less than about 0.05% by weight of toxins (endotoxins). Traditional bacteriophage compositions that were known to be inefficacious in vivo were not host-specific, typically were not purified, usually were toxic and typically were not virulent in vivo. The bacteriophage stock compositions prepared according to the present invention are non-toxic and purified to the extent that renders the bacteriophage compositions effective in killing and/or obliterating and/or reducing sufficient numbers of host bacteria in vivo.

According to one embodiment, the semi-solid composition in which the bacteria and the bacteriophage are grown further comprises rich medium suitable to the type of the host bacteria.

According to another embodiment, the pre-incubated mixture comprises bacteria and bacteriophage at a ratio of about $10^8$-$10^9$ bacterial colony-forming units (cfu) to one bacteriophage plaque.

According to yet another embodiment the semi-solid phase comprises hydrocolloid at concentration below 0.3%, preferably at a concentration of 0.25%-0.30%.

According to one currently preferred embodiment the semi-solid phase comprises agar at a concentration of 0.25%-0.30%.

According to another embodiment, the semi-solid culture medium is supported by a solid phase. There are ongoing research efforts for the development of new supportive solid phases suitable for culture growth. Such supportive solid phase may be in the form of beads, grids, micro-carriers and the like. The method of the present invention is not bound to any specific geometry or material that may be used as a supportive solid phase, as long as the main principle of the invention, the favorable growth of the bacteriophage within the semi-solid phase, is kept. Conveniently, the supportive solid phase has a flat shape. Typically, the volume of the supportive solid phase is from about two to ten folds of the total volume of the semi solid composition that is intended to support.

According to one embodiment, the semi-solid culture medium is layered on top of a first supportive solid phase bottom layer to form a second top layer.

According to one embodiment, the supportive solid phase comprises hydrocolloid at a concentration range of 1.0-2.0%.

According to one currently preferred embodiment, the supportive solid phase comprises agar at a concentration range of 1.0-2.0%. According to yet another embodiment the supportive solid phase and the semi-solid composition are incubated to reach bacterial lysis, thereby obtaining a phage lysate.

According to one embodiment, incubation time is in the range of 12-24 h, preferably 14-18 h, and incubation temperature is typically 37° C. Suitable culture conditions and media for bacteria and phages are well known in the art. The advantage of the present invention over the methods known in the art is the ability to culture the bacteriophage and obtain a concentrated lysate on a commercial scale within a semi solid hydrocolloid medium thereby reducing production volumes and lowering costs.

According to one embodiment the bacteriophage stock composition is obtained by sequential serial extractions comprising the steps of:

a. collecting the semi-solid culture medium;

b. adding fresh medium to the semi-solid culture medium to obtain a slurry;

c. mixing the slurry intensively;

d. centrifuging the slurry to obtain a supernatant comprising a crude bacteriophage extract;

e. collecting the obtained crude bacteriophage extract; and f. repeating the aforementioned steps until the phage titer in the crude bacteriophage extract is below $10^{10}$ pfu/ml; wherein a crude bacteriophage extract having a total phage count of at least from about $10^{15}$ to about $10^{16}$ is obtained from about one liter of semi solid composition.

Typically, the phage titer reaches a value of $10^{10}$ pfu/ml or below after multiple serial extractions, commonly after 5-15 sequential extractions. The crude lysate preparation obtained by sequential extractions may be combined or kept separately. The titer of each stock composition is at least $10^{11}$ pfu/ml, preferably in the range of $5 \times 10^{11}$ to $10^{12}$ pfu/ml. The cumulative volume used for such extractions is typically less than 100 liter, or even less than 70 liter.

According to another embodiment a modified, one step extraction procedure is employed, comprising the steps of:

a. collecting the semi-solid culture medium;

b. adding fresh medium to the semi-solid culture medium to obtain a slurry;

c. mixing the slurry vigorously at low temperature for at least 12 h;

d. centrifuging the slurry to obtain a supernatant comprising a crude bacteriophage extract; and e. collecting the obtained crude bacteriophage extract; wherein a crude bacteriophage extract having a phage count from about $10^{15}$ to about $10^{16}$ is obtained from about one liter of semi solid composition.

Typically, the volume of the fresh medium added to the semi-solid culture medium is in the range of 70-100 liters or even less. According to one embodiment the semi-solid culture medium is vigorously mixed at a temperature of 4° C. for about 14-20 h.

The method of producing bacteriophage compositions according to the present invention can be performed in a completely automated manner, as required for commercial production under GMP standards.

Each step of the method, from the preparation of the initial phage-bacterial stock solution to the extraction of the crude phage lysate may be completed without manual intervention. Automation may be applied to each and every step, or it may be restricted to specific steps only as desired or appropriate for the production facility being used. The automated productions permit the possibility of introducing online process assays or other controls as are well known in the art. For example, temperature sensors can monitor the temperature and the bacterial and bacteriophage growth rate can be monitored by turbidity sensors. In addition to automated assays or other controls it is possible to implement a visual control for performance or quality assurance.

According to yet another embodiment, the bacteriophage crude extract is purified from bacterial debris and endotoxins. Purification may be performed by methods known to one skilled in the art. The high phage titers per volume obtained by the method of the present invention make it possible to use well-developed low-volume purifying methods. For example, crude bacteriophage extract can be subjected to ultrafiltration through a membrane or hollow fiber with a molecular weight cut-off of approximately $10^4$ to about $10^7$ daltons, preferably within the range of from about $10^5$ to about $10^6$ daltons. Alternatively, the bacteriophage crude extracts can be subjected to ultracentrifugation using preparations such as cesium chloride (i.e., at a concentration range of from about 60 to about 95 grams per mole), percoll, ficoll, (i.e., at about 50 to about 80%) or sucrose and glycerol (i.e., at about 5% to about 40%). Ultracentrifugation can be carried out at forces within the range of from about 50,000 g to about 90,000 g, preferably from about 60,000 g to about 80,000 g, for 2 or more hours for cesium chloride, sucrose and glycerol, or for example, from about 20,000 g to about 40,000 g, preferably from about 25,000 g to about 35,000 g for 20 to 30 minutes using percoll or ficoll.

In addition, the partially purified bacteriophage extracts can be detoxified by dialysis using the largest pore membrane that retains bacteriophages, where the membrane preferably has a molecular weight cut-off of approximately $10^4$ to about $10^7$ daltons, preferably within the range of from about $10^5$ to about $10^6$ daltons. Alternatively, the bacteriophage extracts can be detoxified using size exclusion chromatography using preparatory columns with an exclusion pore of from about $10^4$ to about $10^7$ daltons, preferably from about $10^5$ to about $10^6$ daltons. The purified bacteriophage stock composition may be further lyophilized.

The purified bacteriophage stock compositions can then be administered to a test animal that has been infected with the respective bacterial microorganism. The virulence of the bacteriophage composition can be determined by comparing the microbial counts of bacteriophage from infected animals versus the microbial counts for non-infected, or control, animals. The bacteriophage compositions having the highest anti-bacterial activity then can be selected.

These purified bacteriophage stock compositions, which have been selected for virulence, can then be formulated into compositions that can be administered in large enough dosage and in adequate frequency to effect arrest or retardation of infection. The above durations and dosages can be determined on a specific basis for each specific type of phage in each specific type of infection in each specific host. Thus, those skilled in the art will recognize that the effective dosage in a mouse will differ from that of a man, and will also vary according to the specific microorganism. The quantitative determinations can be readily determined by one of ordinary skill in the art.

According to another aspect of the present invention, there is provided bacteriophage compositions efficient in killing host bacteria present during an infection, comprising non-toxic bacteriophage stock composition further comprising substances that reduce or abolish bacterial phage-neutralizing activity.

Lipopolysaccharides (LPS) together with lipoproteins and phospholipids, present on the surface of Gram-negative bacteria, possess phage receptor activity. The absorption of specific phage to the host bacteria can be a multi-step process, involving co-operative or sequential interactions of the bacterial receptors with different sites of the phage adsorption apparatus. As a part of the adsorption process, the bacteria have the ability to neutralize the phage activity. Such neutralization process may significantly reduce the efficacy of phage therapy, by reducing the actual phage titer coping with the infectious bacteria. Substances that imitate the receptor's determinant group can inhibit such inactivation by interacting with the phage adsorption apparatus and blocking the recognition sites that cause inactivation. These substances may be proteins, lipids or sugars according to the specific molecular structure of both the bacterial receptor and the phage adsorption mechanism. Bacteriophage compositions comprising such substances would therefore exhibit a more potent antibacterial activity.

The adsorption of phages to bacterial receptors is known to be specific, due to the molecular structure of both the receptor and the phage adsorption mechanism. One system that was studied as an example for such specificity is that of *Pseudomonas* and its related phages, although only few phages and strains of *P. aeruginosa* were studied. From different researches using purified lipopolysaccharide (LPS) it has been inferred that the receptor sites for at least some of theses phages lie in the core-region of the LPS component. For example, purified LPS obtained from *P. aeruginosa* strain BI (BI-LPS) strongly inactivate phage-2 in vitro. It was shown that BI-LPS contains L-rhamnose, D-glucose, and amino sugars as the major carbohydrate components, while the LPS of a spontaneous phage-2 resistant mutant ($BI/2S_2$) does not inactivate the phage and contains less amino sugars than BI-LPS. Treatment of BI-LPS with phage-2 polysaccharide depolymerase resulted in the release of amino sugars, accompanied by the loss of phage neutralizing activity. Furthermore, free monosaccharides inhibited phage inactivation (Castillo F J 1980 Partial characterization of *Pseudomonas* phage 2 receptor. Can. J. Microbiol. 26:1015-1017): D-galactose, D-xylose and N-acetyl-D-glucosamine had the lowest activity, reducing inactivation from a value of 95% in controls without sugar to 50% only when present at a concentration of about 1.4 M; D-glucose, D-mannose, L-rhamnose and 2-deoxy-D-glucose reduced inactivation to 50% when added at 1M concentration; and D-glucosamine found to be more competent reducing inactivation to 50% when present at a concentration of only 0.25-0.3 M. In view of these results and other studies showing similar neutralization of the bacterial phage inactivation by free sugars, (for example, Patel I R and Rao K K 1983. Studies on the *Pseudomonas aeruginosa* $PAO_1$ bacteriophage receptors. Arch microbiol 135:155-157), the present invention discloses the use of this phenomenon in phage therapy, by producing bacteriophage compositions having a better ability to grow on bacteria, as exemplified herein below.

According to one embodiment of the present invention there is provided a bacteriophage composition comprising non-toxic bacteriophage stock compositions, further comprising at least one sugar that reduce or abolish bacterial phage-neutralizing activity. Any sugar that imitates the receptor's determinant group may be used, preferably mono- or disaccharides. The degree of inhibition should increase as the similarity between the sugar and the determinant group in the receptor increases.

According to yet another embodiment, the inhibitory sugar is selected from the group consisting of N-acetyl-D-glucosamine, 2-deoxy-D-glucose, D-glucosamine, D-fructose, D-galactose, lactose, D-mannose, maltose, L-rhamnose, D-xylose, cellobiose (a disaccharide obtained from a partial hydrolysis of cellulose), and sucrose.

According to one embodiment, there is provided a bacteriophage stock composition comprising purified *Pseudomonas aeruginosa* bacteriophage stock composition and inhibitory sugar selected from the group consisting of D-glucosamine, D-mannose and L-rhamnose. According to one currently preferred embodiment D-glucosamine is at a concentration range of 10-100 mM and D-mannose and L-rhamnose are at a concentration range of 100-1000 mM. According to this aspect of the present invention, bacteriophage stock compositions comprising an inhibitory sugar, further formulated for therapeutic use as described herein below, are diluted as to obtain a physiologically acceptable sugar concentration as is known to those skilled in the art.

According to yet another aspect, the present invention relates to pharmaceutical compositions comprising as an active ingredient a therapeutically effective amount of bacteriophage stock composition.

Pharmaceutical compositions according to the present invention can be prepared by admixing a quantity of a purified bacteriophage stock composition with a pharmaceutically acceptable carrier. For example, the compositions of the present invention are administered in the form of injectable compositions. A typical composition for such purpose comprises a pharmaceutically acceptable carrier. For instance, the composition may contain about 10 mg of human serum albumin and from about 20 to 200 micrograms of the bacteriophage stock composition per milliliter of phosphate buffer containing NaCl. When the bacteriophage stock composition comprises sugars according to the present invention, the sugar concentration should be adapted to reach a non-toxic concentration as known to one skilled in the art. Other pharmaceutically acceptable carriers include aqueous solutions, non-toxic excipients, including salts, preservatives, buffers and the like, as described in Remington's Pharmaceutical Sciences, 15th Ed. Easton: Mack Publishing Co. pp 1405-1412 and 1461-1487 (1975) And The National Formulary XIV., 14th Ed. Washington: American Pharmaceutical Association (1975), the contents of which are hereby incorporated by reference. Examples of non-aqueous solvents include propylene glycol, polyethylene glycol, vegetable oil and injectable organic esters such as ethyloleate. Aqueous carriers can include water, alcoholic/aqueous solutions, saline solutions, parenteral vehicles such as sodium chloride, Ringer's dextrose, and the like. Intravenous vehicles include fluid and nutrient replenishers. Preservatives include antimicrobials, anti-oxidants, chelating agents and inert gases. The pH and exact concentration of the various components of the bacteriophage pharmaceutical compositions of the invention can be adjusted according to routine known in the art. See Goodman And Gilman's The Pharmacological Basis For Therapeutics (7th ed.).

Alternatively, the bacteriophage pharmaceutical compositions of the present invention can be in the form of liposomes, lipophilic microcapsules, dendrimers or the like for oral administration to treat systemic infections. Those skilled in the art are capable of preparing the bacteriophage compositions of the present invention in the form of a lipophilic microcapsule, a dendrimer or a liposome using conventional techniques known in the art. The skilled artisan also is capable of providing a bacteriophage composition that can be administered intranasally, rectally, transdermally, topically, or other known routes of administration of medicaments.

The compositions of the present invention can be used to treat mammals having bacterial infections. Suitable bacteriophage-containing compositions can be prepared that will be effective in killing, obliterating or reducing the quantity of any of the bacterial microorganisms using the guidelines presented above.

The compositions of the present invention preferably are administered intravenously, intranasally, orally, etc., in an amount and for a period of time effective to treat the bacterial infection. The expression "treating bacterial infections," as it is used throughout this description, denotes either (i) killing or obliterating sufficient bacterial microorganisms to render the microorganisms ineffective in infecting the host, or (ii) reducing a sufficient quantity of bacterial microorganisms so as the render the microorganisms more susceptible to treatment using conventional antibiotics. Determining an effective amount of host-specific, non-toxic purified bacteriophage composition to be administered in accordance with the present invention entails standard evaluations. An assessment in this regard would generate data concerning bioavailability, absorption, metabolism, serum and tissue levels and excretion, as well as microorganism levels, markers, and cultures. The appropriate dosage and duration of treatment can be ascertained by those skilled in the art using known techniques.

According to one embodiment, bacteriophage compositions prepared according to the present invention can be used to reduce but not entirely obliterate the population of microorganisms, thereby rendering the infectious focus more susceptible to other chemotherapeutic antibiotics and thus reducing in combination therapy duration, side effects, and risks of the latter. Thus, the bacteriophage pharmaceutical compositions of the present invention can be used in combination with known antibiotics such as aminoglycosides, cephalosporins, macrolides, erythromycin, monobactams, penicillins, quinolones, sulfonamides, tetracycline, and various anti-infective agents. Those skilled in the art can refer to the Physician's Desk Reference, 50th Ed (Medical Economics (1996)), or similar reference manuals for a more complete listing of known antibiotics which could be used in combination with the bacteriophage compositions. For example, a bacteriophage composition effective against various strains of *staphylococcus* could be used in combination with a cephalosporin such as Keflex™ or Keftab™ (both from Cephalexin). Those skilled in the art, using the guidelines provided herein, are capable of designing an effective treatment regimen by either using the bacteriophage composition alone or using a bacteriophage composition in combination with antibiotics.

Having now generally describing the present invention, the same will be more readily understood through reference to the following examples, which are provided by way of illustration and are not intended to be limiting of the present invention.

EXAMPLES

Example 1

Preparation of Phase Lysate Having a High Titer

Strains
  Phage strains:
   ATCC 15692-B3
   ATCC BAA-28
  Bacteria: *Pseudomonas aeruginosa* strain PAO-1 (Prof. H-W. Akkermann's collection, Laval University, Quebec, Canada).

Phage Growth

Phage of one of the strains designated above was propagated on *P. aeruginosa* as described herein below under "Obtaining bacteriophage stock composition". Separate plaques were isolated and stored at 4° C. in 50 ml of Phage buffer ($MgCl_2$ 0.1M, $CaCl_2$ 0.1M, NaCl 0.05M, pH 7.5).

Obtaining Bacteriophage Stock Composition

Bacterial culture of *P. aeruginosa* was seeded in 20 ml Tryptic Soy Broth (TSB) (HyLabs, Rehovot) prepared from one bead (HyTransport storage system, HyLabs, Rehovot) and grown with agitation at 240 rpm at 37° C. for 16-18 h. The culture was then diluted with a fresh TSB to 5% culture, and growth was continued until the OD at 650 nm reached a value of 0.7.

Before plating, 1.5 ml (for each plate) of the bacterial culture was centrifuged, the supernatant was discarded, and the pellet was re-suspended in 200 μl of TBS. Single plaques obtained as described herein above were incubated with each re-suspended pellet at room temperature for 30 min. The phage-bacteria mixture was then added to a semi-solid phase comprising agar at a concentration of 0.27%, and the mixture (6 ml) was spread on 10 cm plates pre-prepared with solid phase comprising 25 ml of growth medium (20 g of dry compounds/l) and agar at a concentration of 1.5%. The plates containing bacteria and phage were incubated at 37° C. for 16-18 h, until substantial lysis of the bacterial layer was observed.

The semi-solid phase was then scrapped from the plate, and transferred to a clean container. 20 ml (per semi-solid phase of one plate) of fresh TSB medium was added to the semi-solid phase. The slurry was mixed for at least 30 sec, and then centrifuged at 11 G for at least 30 min. at 4° C. The supernatant was taken for titer measurement according to Standard phage titration by spot-test method, as known to one skilled in the art, and the pellet was subjected to subsequent extraction. This extraction procedure was repeated 11 times, with additional 20 ml that were added to the pellet obtained after each extraction step.

Figure 1:
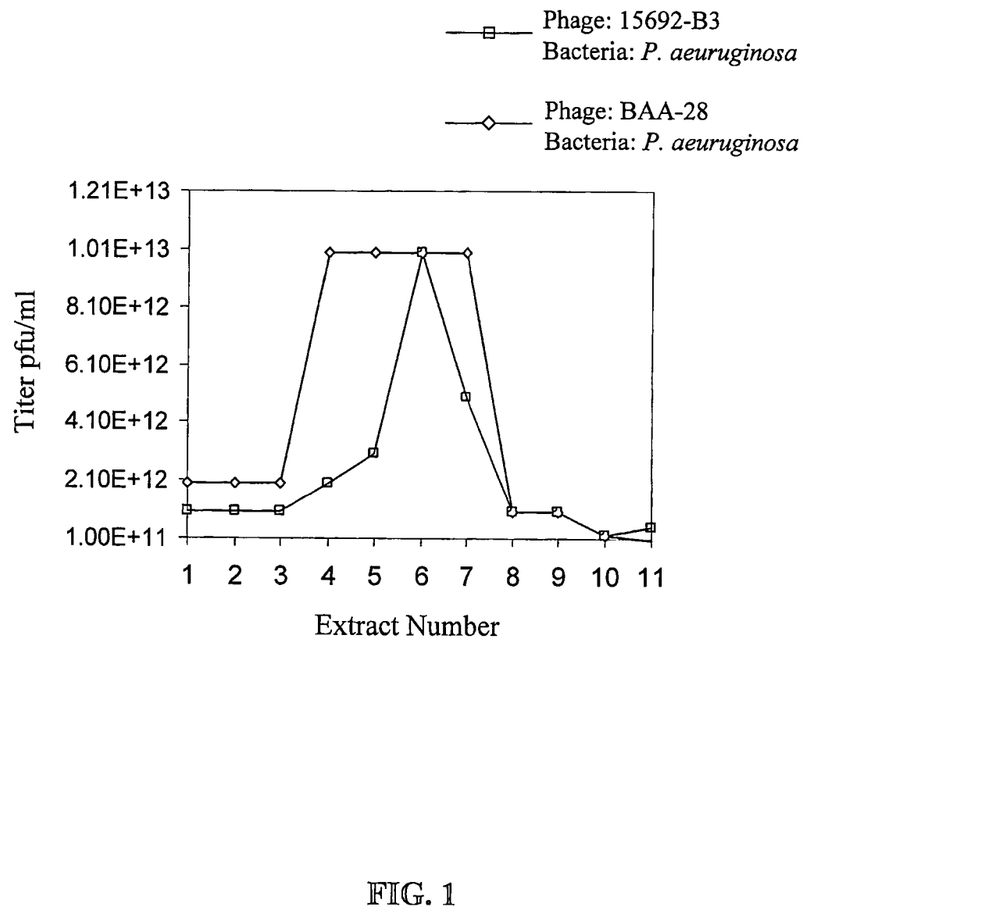
FIG. 1 describes the phage titer obtained in serial extractions where bacteriophages are grown by the method of the present invention.

As shown in FIG. 1, the titer after 11 subsequent extractions was still in the range of $10^9$ to $10^{10}$. Total extraction volume was only 220 ml, and the titer of the stock composition was $4.4 \times 10^{12}$ pfu/ml for phage strain BAA-28 and $2.3 \times 10^{12}$ pfu/ml for phage strain 15692-B3.

Example 2

Intermediate Scale Preparation of Bacteriophage Composition

Figure 2A:
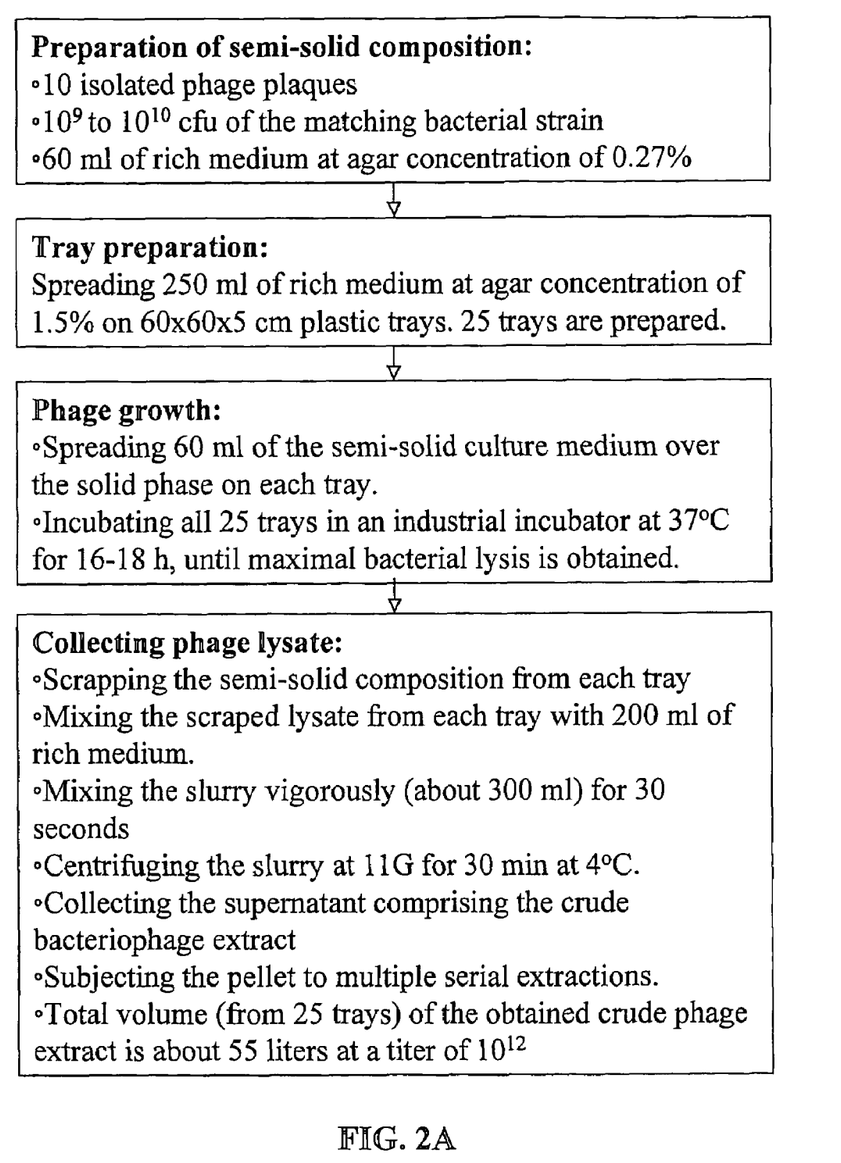
FIG. 2A describes the preparation of bacteriophage crude extract and FIG. 2B describes the purification of the bacteriophage crude extract to obtain bacteriophage stock composition.
Figure 2B:
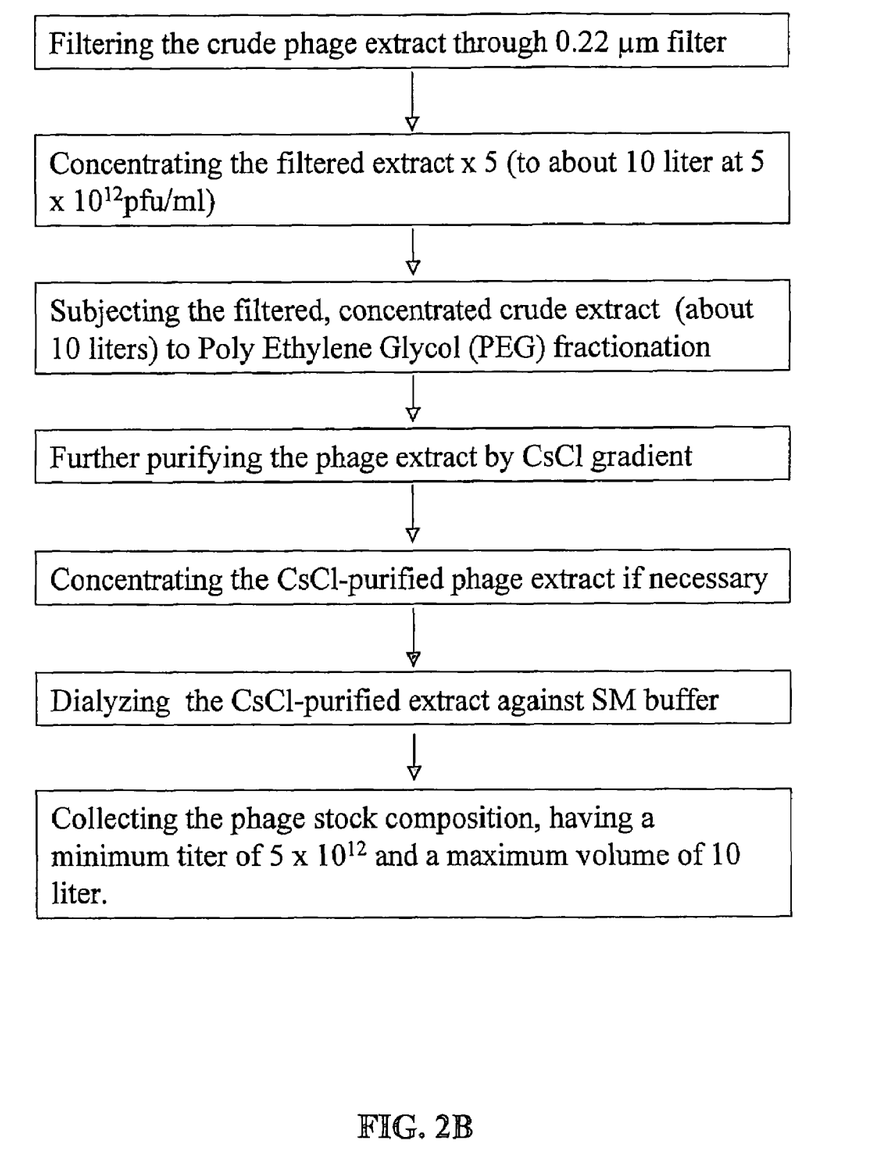

FIG. 2 gives a schematic description of the procedure for manufacturing bacteriophage stock compositions. As shown in FIG. 2A, operation volumes according to the method of the present invention are very low: for obtaining 10 liter of final product at the high titer of $5 \times 10^{12}$ pfu/ml maximum operating volume is about 50 liters. Total phage count in such stock composition is in the order of magnitude of $10^{16}$.

The number of phages required to treat a specific infection depends on the cause of the infection (bacteria type) and on the infection stage (number of bacteria). However, a common rule in bacteriophage therapy is that the amount of phages should be about 100 times the bacterial count. Good treatment may be achieved by application of phage composition at $10^{10}$ to $10^{13}$ pfu/Kg body weight/day, preferably at $10^{11}$ to $10^{12}$ pfu/Kg body weight/day. One run of an intermediate scale procedure as depicted according to FIG. 2, is therefore sufficient to provide about 200-1000 daily doses (the required dose per person).

According the present example, the phage lysate is purified by filtration, Poly Ethylene Glycol (PEG) fractionation and CsCl gradient purification, providing pure bacteriophage stock composition. Nevertheless, the small volume of the crude phage lysate (about 10 liters) make it possible to use many other methods of purification known in the background art.

Example 3

Reduction of Bacterial Phage-Neutralization Activity

Strains
  Phage strains:
   ATCC 15692-B1
   ATCC 15692-B3
  Bacteria: *Pseudomonas aeruginosa* strain 15692 (ATCC)

Obtaining Bacteriophage Stock Composition

Purified bacteriophage stock compositions were obtained according to the procedure detailed in example 1 herein above. Control compositions were extracted with TSB buffer. Compositions with enhanced bacteriophage growth were extracted with TSB buffer containing 45 mM D-glucosamine.

The bacteriophage stock compositions were then tested against *P. aeruginosa* strain 15692 using a ratio of about 1:100 (phage:bacterium), by infecting aliquots of *P. aeruginosa* with the appropriate phage amount, as follows:

Phage 15692 B1 in TSB buffer (control)

Phage 15692 B1 in TSB+45 mM D-glucosamine (enhancing buffer)

Phage 15692 B3 in TSB buffer (control)

Phage 15692 B3 in TSB+45 mM D-glucosamine (enhancing buffer)

After a short incubation at room temperature for about 15 min, each aliquot was diluted with a fresh TSB to about 5% culture.

After incubation the phage titer in each culture was measured by the spot-test method.

The titer of phage 15692 B3 applied to the bacterial culture in a control, TSB buffer, was $10^{10}$ pfu/ml. Same phage applied in enhancing buffer under the exact same conditions reached a titer of $10^{11}$ pfu/ml. Following the same pattern, phage 15692 B1 applied in control TSB buffer reached a titer of $10^{10}$ pfu/ml, while phage stock composition in enhancing buffer containing D-glucosamine reached a hundred fold higher titer of $10^{12}$ pfu/ml.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

The invention claimed is:

1. A method for intermediate to large scale production in a semi-solid culture medium of stock compositions of bacteriophage having a titer of at least $10^{11}$ pfu/ml and a total yield of at least $10^{15}$ total pfu comprising:
   (a) growing bacteriophage in a semi-solid culture medium comprising
       (i) a pre-incubated mixture of at least one bacterial strain and at least one phage type and
       (ii) a hydrocolloid at a concentration below 0.3% wherein the semi-solid culture medium is supported by a solid phase;
   (b) incubating the semi-solid culture medium to reach bacterial lysis, thereby obtaining a phage lysate; and
   (c) extracting a crude bacteriophage extract from the semi-solid culture medium, using an extraction medium, wherein the crude bacteriophage extract is obtained by sequential serial extractions and wherein the titer of the crude bacteriophage extract is at least $10^{11}$ pfu/ml and the bacteriophage yield is at least in the order of magnitude of $10^{15}$ to $10^{16}$ total pfu.

2. The method according to claim 1, wherein the volume of the semi-solid culture medium is in the range of 1-20 liters.

3. The method according to claim 1, wherein the total volume of the extraction medium is in the range of 20 to 100 fold the volume of the semi-solid culture medium.

4. The method according to claim 1, wherein the semi-solid culture medium comprises a hydrocolloid at a concentration of 0.25%-0.30%.

5. The method according to claim 1, wherein the hydrocolloid is selected from the group consisting of agar, agarose, starch, pectin, carrageenan, alginate, gelatin, gellan, konjak mannan, xanthan and gum, and combinations thereof.

6. The method according to claim 5, wherein the hydrocolloid is agar.

7. The method according to claim 1, wherein the pre-incubated mixture comprises bacteria and bacteriophage at a ratio of from about $10^8$ to about $10^9$ bacterial colony forming units to one bacteriophage plaque.

8. The method according to claim 1, wherein the solid phase comprises a hydrocolloid at a concentration range of 1.0-2.0%.

9. The method according to claim 8 wherein the solid phase comprises agar at a concentration range of 1.0-2.0%.

10. The method according to claim 1, wherein the volume of the solid phase is from about two to about ten fold the total volume of the semi-solid culture medium that it is intended to support.

11. The method according to claim 1 wherein the titer of the crude bacteriophage extract is in a range of $5 \times 10^{11}$ to $10^{12}$ pfu/ml.

12. The method according to claim 1 further comprising purifying the crude bacteriophage extract to obtain a bacteriophage stock composition by a method selected from the group consisting of fractionation by PEG, CsCl gradient centrifugation, filtration, ultra-filtration, and column chromatography.

13. The method according to claim 12 wherein the purified bacteriophage stock composition is lyophilized.

14. The method according to claim 8 wherein the volume of the solid phase is from about two to about ten fold the total volume of the semi-solid culture medium that it is intended to support.

15. The method according to claim 9 wherein the volume of the solid phase is from about two to about ten fold the total volume of the semi-solid culture medium that it is intended to support.

16. The method according to claim 7, wherein the pre-incubated mixture further comprises a rich medium.

17. The method according to claim 1, wherein the sequential serial extraction comprises the steps of:
   (a) collecting the semi-solid culture medium;
   (b) adding fresh medium to the semi-solid culture medium to obtain a slurry;
   (c) mixing the slurry intensively;
   (d) centrifuging the slurry to obtain a supernatant comprising a crude bacteriophage extract;
   (e) collecting the obtained crude bacteriophage extract; and
   (f) repeating the aforementioned steps until the phage titer in the crude bacteriophage extract is at or below $10^{10}$ pfu/ml; wherein a crude bacteriophage extract having a total phage count of at least from about $10^{15}$ to about $10^{16}$ is obtained from about one liter of semi solid composition.

18. The method according to claim 1 wherein said stock compositions further comprise at least one sugar that reduces bacterial phage-neutralizing activity.

19. The method according to claim 18 wherein said sugar is present in said stock compositions at a concentration in the range of 0.1 to 1 M.

20. The method according to claim 18 wherein the sugar is selected from the group consisting of N-acetyl-D-glucosamine, 2-deoxy-D-glucose, D-glucosamine, D-fructose, D-galactose, lactose, D-mannose, D-xylose, maltose, L-rhamnose, cellobiose, and sucrose.

21. The method according to claim 20 wherein the sugar is selected from the group consisting of D-glucosamine, D-mannose, and L-rhamnose.

22. The method according to claim 1 wherein said incubating the semi-solid culture medium is carried out at a temperature of 37° C. for a period of 12 hours to 24 hours.

23. The method according to claim 22 wherein said incubating the semi-solid culture medium is carried out at a temperature of 37° C. for a period of 14 hours to 18 hours.

* * * * *